(12) United States Patent
van Dun

(10) Patent No.: US 8,809,631 B2
(45) Date of Patent: Aug. 19, 2014

(54) SCREENING METHOD FOR SELECTING PLANTS THAT SHOW REDUCED WOUND-INDUCED SURFACE DISCOLOURATION AND PLANT AND PLANT PARTS THUS OBTAINED

(75) Inventor: Cornelis Maria Petrus van Dun, Roosendaal (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 1433 days.

(21) Appl. No.: 11/650,833

(22) Filed: Jan. 8, 2007

(65) Prior Publication Data
US 2007/0180573 A1    Aug. 2, 2007

(51) Int. Cl.
*A01H 1/00* (2006.01)
*A01H 5/00* (2006.01)
*A01H 5/10* (2006.01)
*C12N 15/01* (2006.01)

(52) U.S. Cl.
USPC ............................ 800/305; 800/260; 435/410

(58) Field of Classification Search
USPC .................................................. 800/260, 270
See application file for complete search history.

(56) References Cited

U.S. PATENT DOCUMENTS

2005/0268360 A1    12/2005    Gibson

FOREIGN PATENT DOCUMENTS

| WO | WO 94/03607 | 2/1994 |
| WO | 97/39350 | 10/1997 |

OTHER PUBLICATIONS

Laidou et al. J. Phytopathology 149: 457-461, 2001.*
Hanotel et al. Postharvest Biology and Technology 5: 199-210, 1995.*
Lopez-Galvez et al. Postharvest Biology and Technology 8: 179-190, 1996.*
U.S. Appl. No. 12/168,484.*
U.S. Appl No. 12/631,385.*
Hanotel et al. Postharvest Biol. and Technology 5: 199-210, 1995.*
Saltveit et al. Postharvest Biology and Technology 27: 277-283, 2003.*
Hisaminato et al (Biosci. Biotechnol. Biochem. 65(5): 1016-1021, 2001).*
Saltveit et al (Postharvest Biology and Technology 27: 277-283, 2003).*
Hanotel et al (Postharvest Biology and Technology 5: 199-210, 1995).*
Choi et al (Postharvest Biology and Technology 37: 47-55, 2005).*
T. Demeke, et al., Effect of Germination, Seed Abrasion and Seed Size on Polyphenol Oxidase Assay Activity in Wheat, Plant Breeding (2001) vol. 120, pp. 369-373.
Anna M. Girelli, et al., Inhibition of Polyphenol Oxidases Activity by Various Dipeptides, J. Agric. Food Chem. (2004) vol. 52, pp. 2741-2745.
Hiromi Hisaminato, et al., Relationship Between the Enzymatic Browning and Phenylalanine Ammonia-lyase Activity of Cut Lettuce, and the Prevention of Browning by Inhibitors of Polyphenol Biosynthesis, Biosci. Biotechnol. Biochem. (2001) vol. 65, No. 5, pp. 1016-1021.
Anne H. Rathjen, et al., Characterisation of a Variegated Grapevine Mutant Showing Reduced Polyphenol Oxidase Activity, Aust. J. Plant Physiol. (1992) vol. 19, No. 1, pp. 43-54.
International Preliminary Report on Patentability, Jul. 17, 2008, PCT/EP2004/000226.

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

Provided is a method for screening a population of plants or plant parts for the presence therein of individuals that show a reduced wound-induced surface discolouration as compared to a control plant or plant part, which method comprises providing a population of plants or parts of the plants from the population; creating a wound surface on the plants or plant parts to be screened and on the control plants or plant parts; incubating the wound surfaces to allow for discolouration to occur therein or thereon; observing the wound surface discolouration in or on the plants or plant parts; comparing the observed wound surface discolouration in or on the plants or plant parts to be screened with the discolouration that is observed on or in the control plant or plant parts. The plants thus selected are also provided.

11 Claims, 11 Drawing Sheets
(11 of 11 Drawing Sheet(s) Filed in Color)

SCREENING METHOD FOR SELECTING PLANTS THAT SHOW REDUCED WOUND-INDUCED SURFACE DISCOLOURATION AND PLANT AND PLANT PARTS THUS OBTAINED

CROSS-REFERENCE TO RELATED APPLICATIONS

This application claims priority to EP application no. 2006075039, filed Jan. 6, 2006. The foregoing application, all documents cited in the foregoing application ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a method for screening a population of plants or plant parts for the presence therein of individuals that show a reduced wound-induced surface discolouration as compared to a control plant. The invention also relates to plants and parts derived therefrom showing an absent or reduced wound-induced surface discolouration obtained by means of this method and to parts and progeny thereof.

BACKGROUND OF THE INVENTION

Due to increasing demand, processing of fresh produce, in particular lettuce, has expanded significantly over recent years. The harvesting and processing of lettuce involves extensive cutting of the leaves, which induces a strong wound response. This wound response leads to a rapid deterioration of the processed product. This deterioration is manifested by discolouration due to enzymatic browning or pinking at and around the wound surface, respiration and desiccation due to transpiration. The enzymatic browning or pinking is considered of significant importance in determining directly or indirectly the overall quality of the fresh cut, packaged lettuce.

Moreover, as a consequence of the deterioration, microorganisms can significantly increase in number, which may compromise food safety. The highly perishable nature of processed lettuce leads to a strong off-colour, off-odour and off-texture perception by the consumer, which has hampered faster growth of the so called convenience market.

In order to inhibit the deterioration process, many chemical or physical post-harvest treatments have been developed, which can be applied to decelerate the deterioration of the processed lettuce. Amongst these are the packaging of fresh cut lettuce under a modified atmosphere, application of edible coatings, heat shock treatment, and addition of chemicals which inhibit the enzymatic browning. When fresh cut lettuce is packaged under an atmosphere of reduced oxygen at low temperatures, the enzymatic browning can be substantially reduced. However such modified, low oxygen environment leads to anaerobic respiration, which creates an off-flavour and off-odour of the produce that is perceived as very unattractive.

Edible coatings are thin layers of materials, which act as a physical insulation barrier and which effectively protect the produce from different forms of deterioration such as evaporation and browning. These coatings can for example be made of resins, polysaccharides or protein.

It has further been demonstrated that browning of fresh cut lettuce can be prevented by applying a brief a heat shock of 90 seconds at 45° C., immediately after processing. Possibly, the heat shock diverts protein biosynthesis from the enzymes involved in discolouration towards heat shock proteins thereby reducing the enzymatic browning capacity. Alternatively, the effect of heat shock treatment on browning may be explained by thermosensitivity of enzymes involved in the discolouration pathway.

Chemicals which can be applied can be, for example, reducing agents like vitamin C, chelating agents like EDTA, complexing agents like cyclodextrin and enzymatic inhibitors like L-cysteine. Application of chemicals in fresh food obviously involves food safety issues and requires regulatory approval. Combinations of the post-harvest technologies described above can be thought of and ultimately the applied procedure is a trade-off between technological efficacy, cost and food safety.

Irrespective of the technology applied, improvement of post-harvest quality of processed lettuce will come at a cost; therefore, a clear need in the art exists to provide alternatives that eliminate or reduce the need to apply physical or chemical post-harvest technologies.

SUMMARY OF THE INVENTION

It is the object of the present invention to provide a screening method to select for plants that show a reduced wound-induced discolouration response to provide plants and progeny derived therefrom that are resistant to post-harvest processing disorders such as enzymatic browning or pinking. It is a further object of the invention to provide plants that show a significantly reduced pinking or browning discolouration upon wounding. Discolouration upon wounding can also be visible in parts of the plants, such as stems, seeds, fruits, leaves, flowers, tubers and shoots. It is thus a further object of the invention to provide a screening method to select for plants that show a reduced wound-induced discolouration response in their plant parts.

In one embodiment, the invention provides a method of screening test plants or plant parts for a plant having reduced wound-induced surface discolouration as compared to a control plant or plant part, which method comprises:

creating a wound surface on a test plant or a part thereof;

incubating the wound surface to allow for discolouration to occur;

comparing the discolouration of the wound surface of the test plant or part thereof with discolouration in a control plant or part thereof to identify a plant having reduced wound-induced surface discolouration as compared to the control plant.

A defining characteristic of the control plant is that a leaf disc from the control plant shows pink discolouration at the edges when incubated between two sheets of wetted filter paper for 7 days at 5° C.

The invention thus provides a method for screening a population of plants or plant parts for the presence therein of individuals that show a reduced wound-induced surface discolouration as compared to a control plant or plant part, which method comprises:

providing a population of plants or parts of the plants from the population;

creating a wound surface on the plants or plant parts to be screened and on the control plants or plant parts;

incubating the wound surfaces to allow for discolouration to occur therein or thereon;

observing the wound surface discolouration in or on the plants or plant parts;

comparing the observed wound surface discolouration in or on the plants or plant parts to be screened with the discolouration that is observed on or in the control plant or plant part to identify plants or plant parts that show no discolouration or a discolouration that is reduced as compared to the control plant or plant part.

The method of the invention can be used for any plant that may be subject to discolouration, but is in particular useful for produce, in particular vegetables or fruits, or for flowers. The method is inter alia suitable for leafy vegetables, such as lettuce, for tubers, like potato or sweet potato, for roots, such as celeriac, for shoots, such as witloof, or for mushrooms. The method can furthermore be used for fruits, such as apple, banana, avocado, peach, pear, apricot, mango, eggplant and for flowers or flower stems, such as gerbera stems, chrysanthemum flowers, artichoke bottoms etc.

The screening method of the invention is intended for identifying plants that have a reduced wound-induced surface discolouration in one or more of their parts or tissues. For the screening, it is therefore very practical to use the part or tissue that is prone to discolouration. In lettuce, this may be the leaf or a part thereof, such as a punch, in banana, slices of the peeled fruit can be suitably used, and in flowers, slices of the stem are a very practical test vehicle.

When plant parts other than leaf tissues are screened (for example, fruits or stems), a control plant or part thereof will preferably be the same part as that of the test plants. The control will show average discolouration of its wounded surface, meaning that discolouration which is typical and representative of the plant type.

In a specific embodiment the method is particularly useful for selecting plants belonging to the family Asteraceae, in particular, plants of the genus *Lactuca* and in particular to the species *Lactuca sativa* or plants belonging to the genus *Cichorium* and in particular to the species *Cichorium intybus* and *Cichorium endivia* that show an absence or reduction of wound-induced surface discolouration.

The plant population that is screened with the method of the invention can be any plant population, but is preferably a non-naturally occurring plant population that has many different members to increase the chances of identifying a plant having reduced wound-induced discolouration. Such a population of non-naturally occurring plants can be made by mutagenic treatment using, for example, chemicals and/or irradiation and is then called a mutant plant population. Alternative populations are germplasm collections, which are collections of plants having natural variation. A population of transgenic plants can also be used.

The method of the invention is suitably performed with plant parts having a wound surface. Very useful test samples are discs that are punched from a leaf, the so-called leaf discs. Alternatively, the midrib tissue of veined leafy vegetables can be used. Suitably, discs are cut from such ribs.

Incubation takes suitably place in an aqueous environment. The method of the invention can be very well practised with leaf discs that are incubated on or between wetted filter paper.

The discolouration response is then very well visible around the edges of the wound on the paper. In plants of the genera *Lactuca* and *Cichorium*, the discolouration is the pinking response.

Alternatively, the aqueous environment comprises water or a solution. In a specific embodiment that will be further illustrated below the solution contains L-3,4-dihydroxyphenylalanine. This compound is converted to the production of the black pigment melanin by the enzyme polyphenol oxidase. Alternative compounds that can be used include, but are not limited to, chlorogenic acid, isochlorogenic acid, L-tyrosine, and catechol.

In another embodiment, the invention provides a method of producing a plant having reduced wound-induced surface discolouration as compared to a control plant, which method comprises:

crossing plants to produce a population of test plants;

creating a wound surface on each test plant or a part thereof;

incubating the wound surface to allow for discolouration to occur;

comparing the discolouration of the wound surface of the test plants or parts thereof with discolouration in a control plant or part thereof;

selecting a plant having reduced wound-induced surface discolouration as compared to a control plant.

The invention further relates to a non-naturally occurring plant showing a reduced wound-induced surface discolouration, which plant is obtainable by subjecting a population of plants to the screening method of the invention and selecting plants from the population that show no surface discolouration in the screening or show a surface discolouration in the screening that is reduced as compared to a control plant.

The plant is a suitably a leafy vegetable plant, more in particular a plant which belongs to the genus *Lactuca* and in particular to the species *Lactuca sativa* or a plant which belongs to the genus *Cichorium* and in particular to the species *Cichorium intybus* and *Cichorium endivia*.

Preferably, the plant of the invention is identified in the screen and subsequently selected as having a reduced or absent wound-induced surface discolouration but is subsequently tested to determine whether it has a normal habit. More in particular, the plant should preferably not show negative pleiotropic effects.

The invention further relates to plants having a reduced or absent wound-induced surface discolouration and that are obtainable by crossing a plant of the invention with another plant of the same species. The feature "reduced or absent wound-induced surface discolouration" can thus be brought into other plants that originally do not have the feature. Whether the plants resulting from such a cross are indeed plants of the invention can be tested by subjecting these plants to the screening method of the invention. Preferably, the plants that are selected as plants of the invention are then also tested for having a normal habit.

The invention further relates to progeny of a parent plant of the invention that retains the absence or reduction of wound-induced leaf discolouration as found in the parent plant. Such progeny may be many generations removed from the parent. As long as the feature "reduced or absent wound-induced surface discolouration" is retained, the plant is a plant of the invention.

The invention further relates to parts of the plants of the invention. The plants parts like lettuce or endive heads or leaves are usually the parts that have a cut surface that may be subject to discolouration.

Plant parts of the invention can be used in tissue culture to regenerate plants that retains the absence or reduction of wound induced leaf discolouration as found in the plant from which the tissue for the tissue culture is derived. Such regenerated plants are also part of this invention.

The invention further relates to seed of a plant of the invention. From the seed plants can be grown that also have the feature "reduced or absent wound-induced surface discolouration". Whether or not the seeds and thus the plants grown therefrom have retained that feature can be tested in the screening method of the invention. The invention also relates to further generation seeds that retain the absence or reduction of wound induced leaf discolouration as found in the original seeds.

The invention is commercially very interesting for the processed vegetable market. As explained above, discolouration of produce, in particular fresh fruits and vegetables, is considered undesirable since the discoloured product is rejected by the consumer. The feature "reduced or absent wound-induced surface discolouration" of the invention is thus suitable found in processed vegetable products, like cut lettuce, endive or witloof or combinations thereof. When screened using the method of the invention, processed vegetables of the invention show no or a limited wound-induced leaf discolouration. All processed vegetables, in particular processed lettuce, endive and witloof that meet the screen are part of the invention since they are demonstrated to have a modification leading to a reduced PAL and/or PPO dependent metabolic flux.

BRIEF DESCRIPTION OF THE DRAWINGS

The present invention will be further illustrated in the Examples that follow, which are not intended to limit the invention in any way. The Examples refer to lettuce but instead of lettuce, other produce plants or parts thereof, in particular fresh fruits and vegetables, can be used. In the Examples reference is made to the following figures.

This patent file contains at least one photograph executed in color. Copies of this patent with color photographs will be provided by the U.S. Patent and Trademark Office upon request and payment of the necessary fee.

The output signal of the screen is a brown or pink discolouration, depending on the conditions applied, of the wound surface diagnostic for post-harvest browning and pinking. This is inferred from the fact that the output signal is completely inhibited by cinnamaldehyde and L-cysteine which are specific inhibitors of PAL and PPO, respectively.

Figure 2:
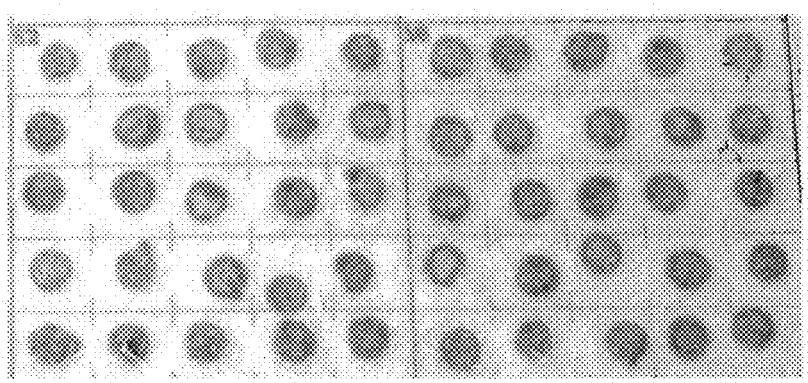

FIG. 2: Representative image of the output phenotype of the screen based on pink discolouration of leaf discs. Leaf discs of lettuce plants (1 disc per plant) are arrayed between wetted filter papers and incubated at 5° C. for 7 days. A pink discolouration can clearly be observed around each leaf disc at the wound surface.

Figure 3:
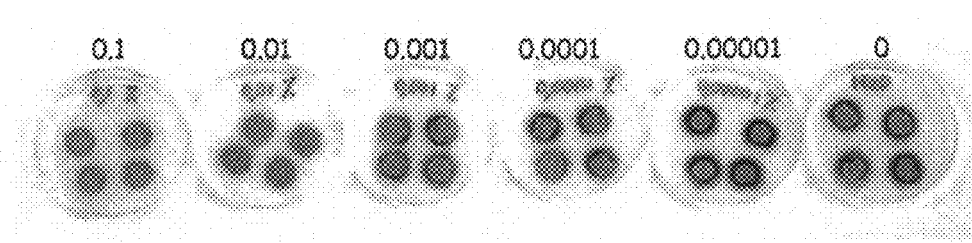

FIG. 3: The leaf disc pinking assay (4 discs per dish) carried out in the presence of different concentrations of the PAL inhibitor cinnamaldehyde. The number above each dish shows the % of cinnamaldehyde used.

Figure 4:
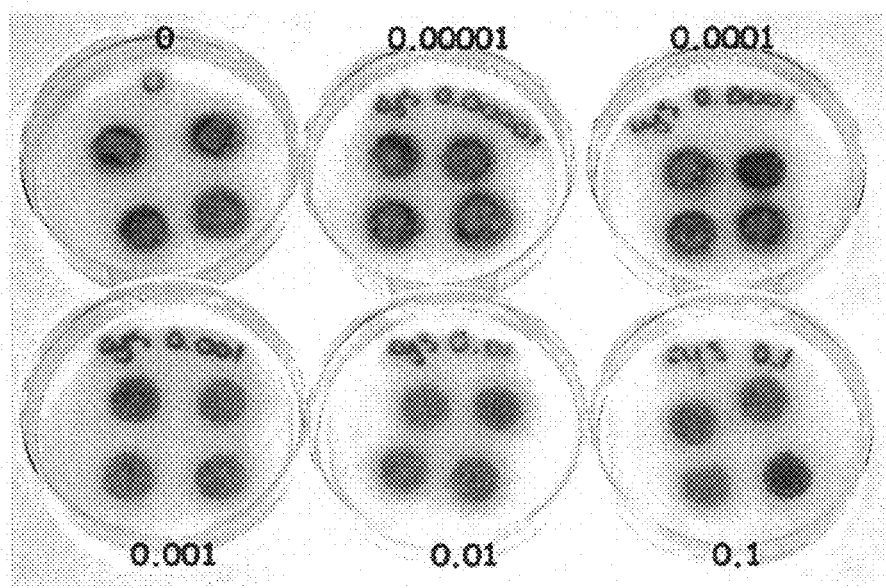

FIG. 4: Inhibitory effect of the PPO inhibitor L-cysteine on the pink discolouration of lettuce leaf discs (4 discs per dish) incubated between wetted filter papers. The number above each dish shows the % of L-cysteine used.

Figure 5:
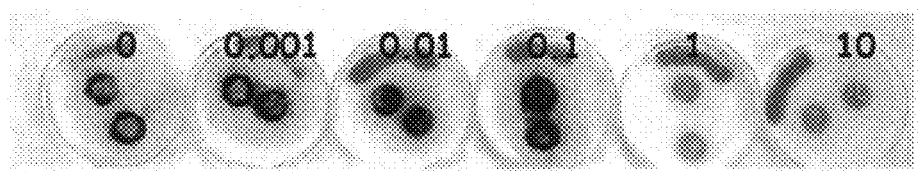

FIG. 5: Inhibitory effect of the PPO inhibitor L-cysteine on the black discolouration of lettuce leaf discs (4 discs per dish) incubated between wetted filter papers in the presence of 1.5 mM L-DOPA. The number above each dish shows the mM concentration of L-cysteine used.

Figure 6:
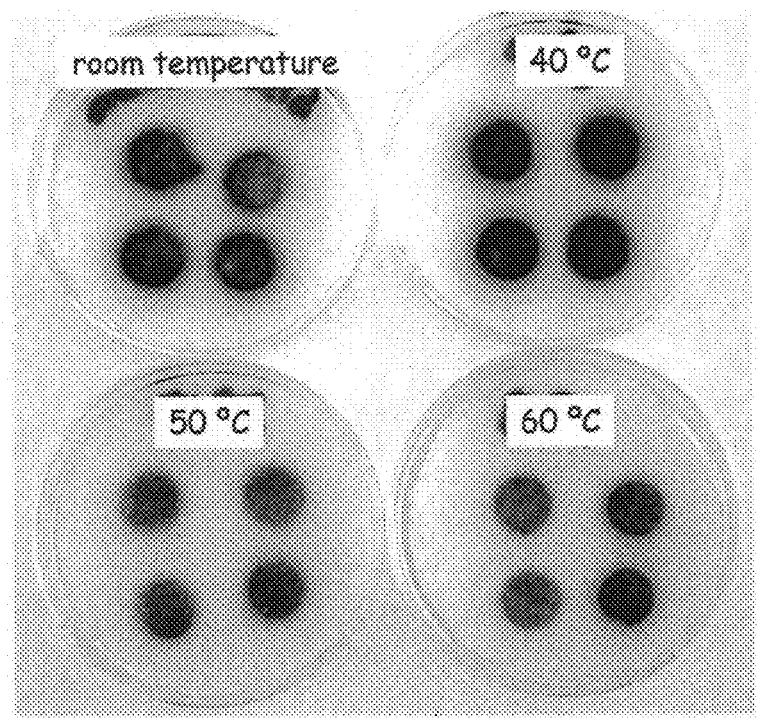

FIG. 6: The effect of heat shock pre-treatment on lettuce leaf disc pinking. The heat shock was applied for 90 seconds on intact leaves at the temperature indicated on each dish.

Figure 7:
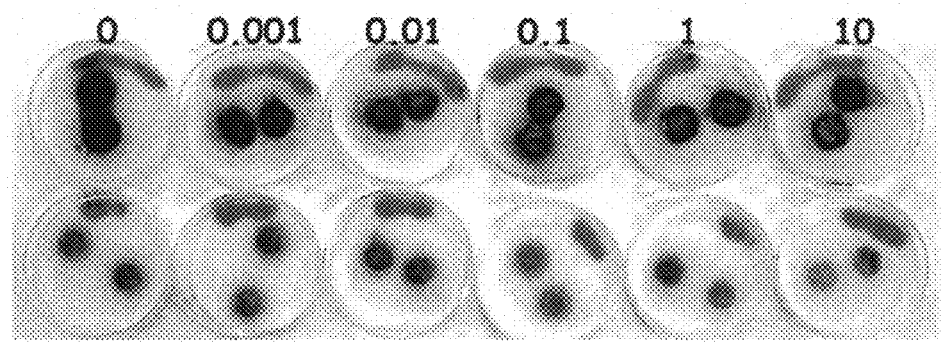

FIG. 7: Conversion of the pink dye formed by the wound response of lettuce to a colourless compound by L-cysteine. The upper row of dishes shows the L-DOPA assay whereas the lower row of dishes shows the pinking assay. The lower of the two discs in each dish was treated with L-cysteine after the wound response had been completed. The concentration of L-cysteine used are 0, 0.001, 0.01, 0.1, 1 and 10 mM which is indicated above.

Figure 8:
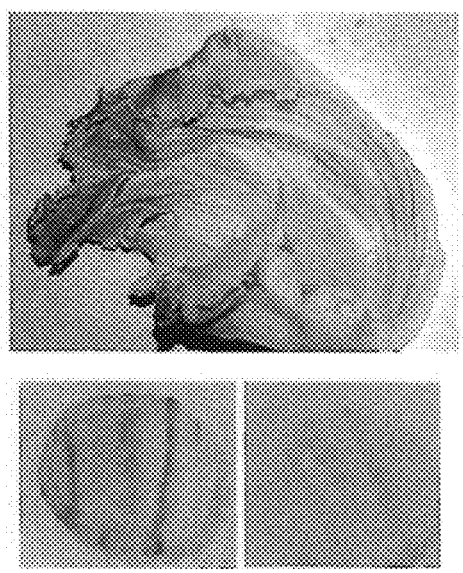

FIG. 8: Reduction of pinking in filed grown lettuce by L-cysteine. The upper panel shows typical pinking symptoms of a lettuce leaf taken from a plant which was extremely stressed by water logging. The main veins show the presence of a pink dye. The lower right panel shows a disc taken from the leaf showing pinking symptoms after treatment with 1 mM L-cysteine for 30 minutes at room temperature. The lower left panel shows a similar leaf disc after treatment with water for 30 minutes at room temperature.

FIG. 9A: Phenotypic analysis of individual lettuce M2 plants (grouped in pools) for leaf disc discolouration according to the method described by this invention. A total of 138 samples out of 12000 is shown in this panel of which the one indicated by an arrow showed a strongly reduced pinking discolouration. FIG. 9B: Re-testing of the selected individual indicated in panel A confirmed the near absence of the formation of the pink discolouration (sample in the middle position) as compared to control samples which show a clear discolouration response.

Figure 10:
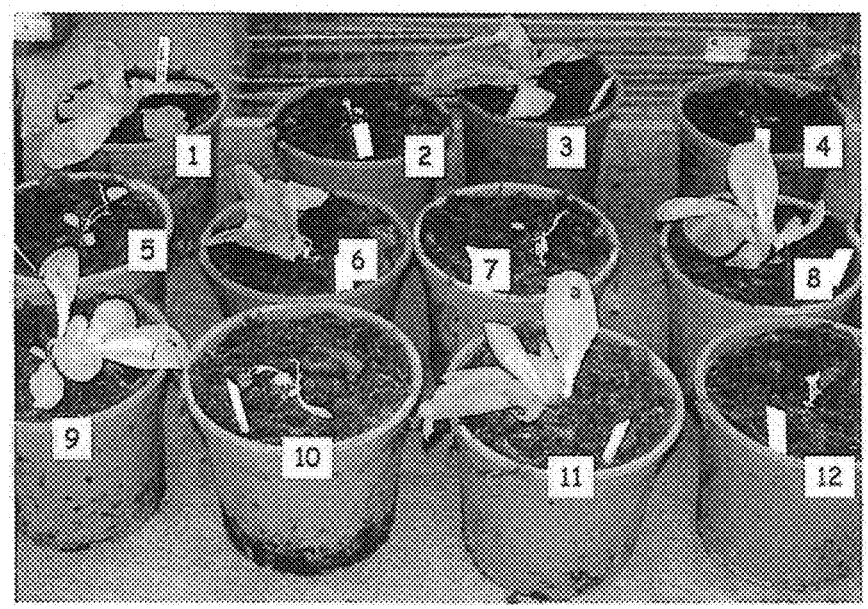

FIG. 10: Phenotypes of M2 lettuce plants. The plants labelled 1, 2, 4, 5, 7, 10 and 12 show reduced pink leaf disc discolouration using the assay according to this invention. Plants 3, 6, 8, 9, and 11 are plants which showed a level of pink leaf disc discolouration comparable to the wild type control. Plant 1 is the only example of a mutant which shows a strong reduction in pink discolouration and a normal growth habitus. Plants 2, 4, 5, 7, 10 and 12 show reduced pink discolouration and a dwarfed, bleached phenotype.

Figure 11:
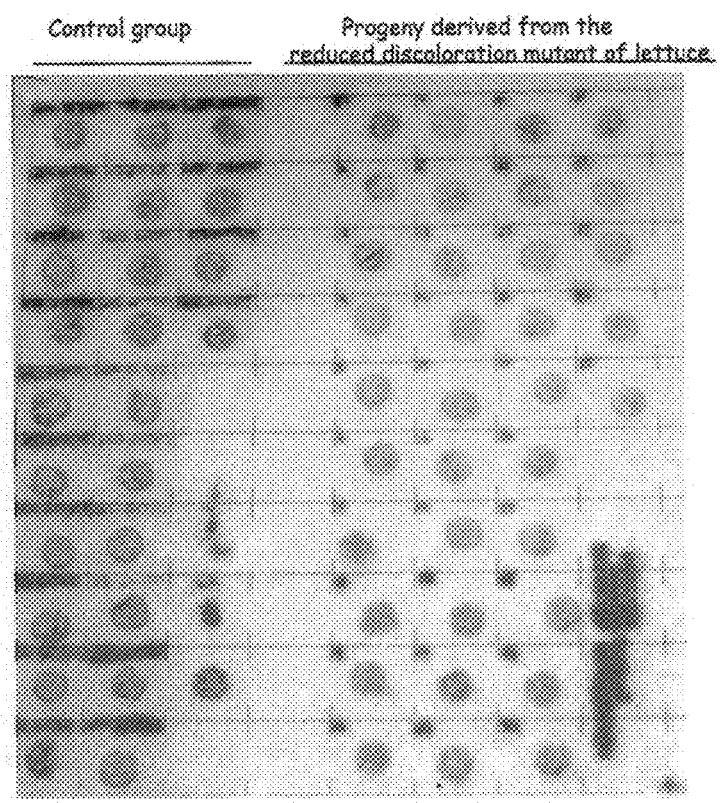

FIG. 11: Progeny testing of a mutant of lettuce showing a reduced discolouration. On the left, 25 control samples are shown which show a normal wound induced discolouration response. On the right, a group of samples is shown which is taken from a series of 35 progeny plants derived from a single mutant which is severely reduced in its wound induced discolouration response.

Figure 12:
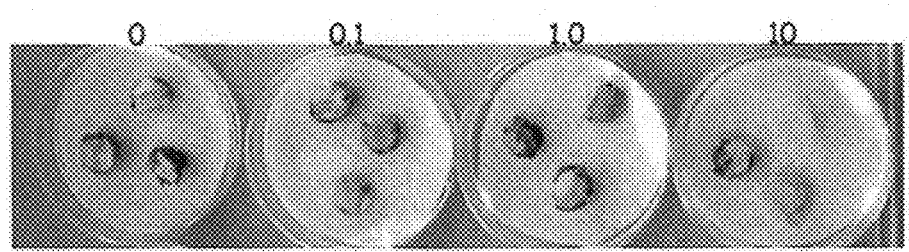

FIG. 12: Representative image of the output phenotype of the screen based on brown discolouration of leaf midrib parts taken from mature lettuce plants. The picture shows lettuce outer leaf midrib tissue discs after incubation for 3 days at 16° C. The typical brown discolouration can clearly be observed at the wound surface. Each dish contains 3 discs taken at different positions of the midrib (green, light green and white). The number above the dish indicates the mM concentration of L-cysteine which was added to the filter.

Figure 13:
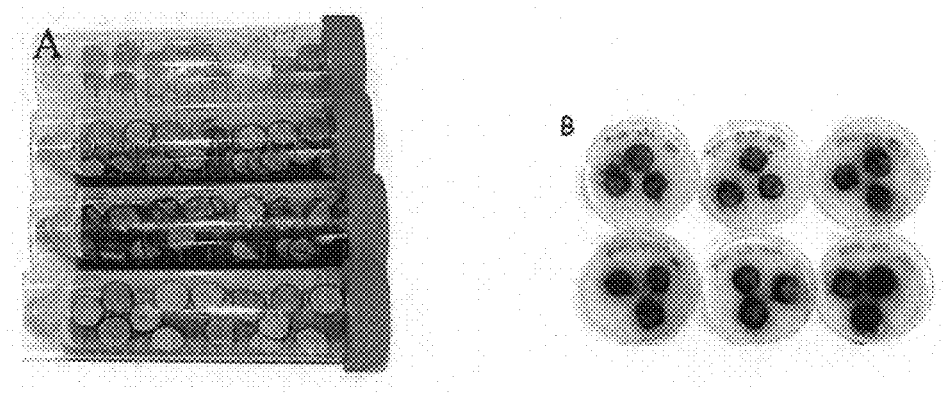

FIG. 13: Conversion of L-DOPA at the lettuce leaf surface into melanin. FIG. 13A shows the assay in a 1.5 mM L-DOPA solution. The upper tube is the negative control, the other 3 tubes are identical. FIG. 13B shows the result of the incubation of leaf discs between wetted filter papers which contain 1.5 mM L-DOPA.

Figure 14:
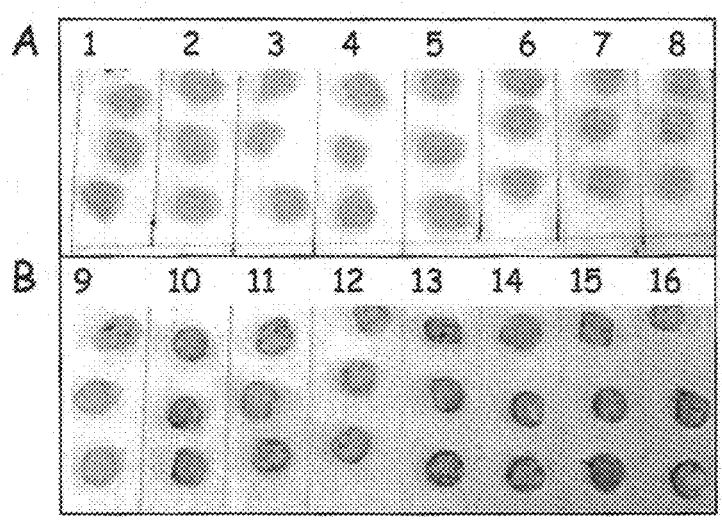

FIG. 14: Progeny testing of a mutant of lettuce showing a reduced wound induced pink discolouration on midrib browning. FIG. 14A shows the midrib discs of 8 progeny plants, numbered 1 to 8 (3 discs per plant) of the reduced pinking mutant. FIG. 14B shows the midrib discs of 8 control plants numbered 9 to 16 (3 discs per plant) which show a normal browning response.

Figure 15:
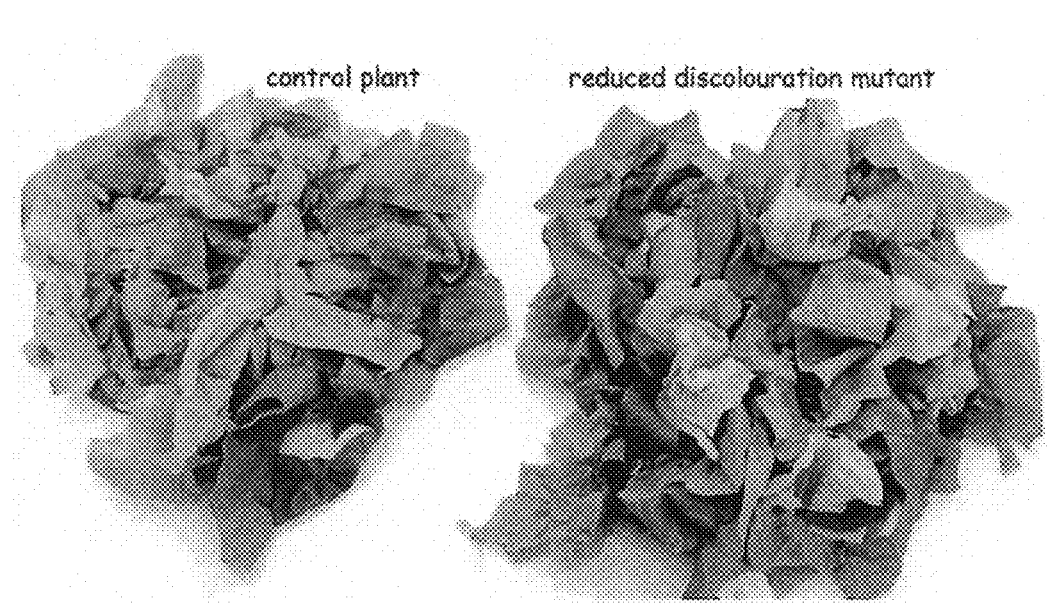

FIG. 15: Assessment of a mutant of lettuce showing a reduced wound-induced pink discolouration or browning response after cutting and packaging under ambient atmosphere. Leaf pieces of the head of a control plant are shown on the left and leaf pieces of the reduced discolouration mutant is shown on the right. The fresh cut leaf material was stored for 6 days at 4° C. The brown discolouration can be clearly observed in the control samples whereas the mutant samples remain unchanged.

DETAILED DESCRIPTION OF THE INVENTION

When lettuce is harvested and processed by cutting, many leaf wound surfaces are generated which leads to a significant response of the plant or plant parts, manifested by a brown or pink discolouration at or adjacent to the wound surface. Pinking can also be observed at sites distant from the wound surface at the midrib of the leaf as well as the butt. Sometimes pinking can also be observed at stages just prior to harvest which is considered to be due to abiotic stress or over-maturity of the crop.

The different forms of discolouration are affected by enzymatic activity, which is strongly enhanced as a consequence of wounding and which generates several forms of polyphenols and reaction products derived therefrom.

An important enzymatic activity involved in the browning reaction is polyphenol oxidase (PPO). PPO activity in relation to enzymatic browning is not restricted to lettuce but has been described for many other plant species to be involved in post-harvest deterioration like in apple, banana and potato. In fact, PPO is widely recognised to be one of the most important enzymes involved in post-harvest deterioration of many processed fresh fruits and vegetables.

For this reason PPO has been the target of many technologies which aim at the reduction or prevention of its activity in order to increase post-harvest quality of food products. PPO catalyses a reaction in which polyphenols residing in the plant tissue are oxidised to give rise to the formation of o-quinones. Subsequently, enzymatic and non-enzymatic reactions lead to the formation of brown or black pigments.

In many plant species PPO is encoded by a small gene family of which the individual members may have different temporal and spatial expression patterns indicative of functional divergence. It has for example been shown that lettuce contains different PPO isoforms in the photosynthetic and vascular tissue of the leaf.

The natural substrate of PPO can differ between the different species. In lettuce, caffeic acid derivatives like chlorogenic and isochlorogenic acid mainly act as PPO substrate.

The level of PPO enzyme is not specifically induced upon wounding of plant tissues but it resides inactively in the chloroplast. Upon wounding PPO activated which is manifested due to the fact that the phenolic substrate residing in the vacuoles is brought into contact with PPO due to tissue disruption.

In lettuce, the production of polyphenols which are the substrate of PPO is induced upon wounding. Therefore the browning potential of lettuce tissue seems not to be limited by the amount of PPO in the leaf tissue but rather by the rate of polyphenol biosynthesis upon wounding.

In this respect the situation may differ between crops. For example, in apple the amount of polyphenols is sufficient to generate a browning response of the fruits within one hour after wounding whereas in lettuce the browning reaction may take a few days due to the fact that in lettuce the polyphenol pool largely needs to be synthesised de novo upon wounding.

The synthesis of polyphenols occurs through a well-characterised biochemical pathway called the phenylpropanoid pathway. The first, committed step of this pathway is catalysed by the enzyme phenylalanine ammonia lyase (PAL, Hahlbrock, K and Scheel, D (1989) Annu. Rev. Plant Physiol. Plant Mol. Biol. 40, 347-369). PAL converts the amino acid phenylalanine synthesised through the shikimate pathway into cinnamic acid.

In lettuce, wounding of leaves leads to a strong induction of PAL gene expression and PAL activity. The formation of polyphenols is correlated with this enzymatic activity which suggests that PAL activity induced by wounding of lettuce is an important factor responsible for browning (Campos, R. et al. (2004) Physiologica Plantarum 121, 429-438 and references therein). However, it is currently unclear which other factors determine the final outcome of the wound-induced discolouration reaction. For example, the activity of peroxidases (POD) has been suggested to be important as well in establishing the final level of discolouration (Fukumoto, L. R. et al. (2002) J. Agric. Food Chem. 540, 4503-4511; Martin-Diana A. et al (2005) Biosci. Biotechnol. Biochem. 69, 1677-1685).

As the enzyme activity depends on the availability of internal hydrogen peroxide, the contribution of POD to discolouration may be limited.

It is further evident that wounding is somehow perceived by the plant and subsequently a signal is generated through a cascade which is currently poorly defined for lettuce. It seems obvious that these activities will primarily be targeted towards wound healing and defence against pathogens. Therefore, it is likely that many genetic factors are involved in mounting the discolouration response of wounded lettuce tissue and each of these are potential targets for genetic modification to reduce or eliminate the wound-induced discolouration.

Most of these genetic factors are currently unknown and for those known to be involved it is unclear to what extent these factors play a specific role in the discolouration reaction or perhaps have a more general function in relation to the wound physiology of the plant.

For example, although wound-induced PAL activity is considered to be determining the browning level of lettuce, products of the phenyl propanoid pathway are known to be involved in inter alia cell wall biosynthesis or defence response as well. Therefore reducing the wound-induced PAL activity in order to reduce browning potential may compromise other functions besides wound-induced browning which may be less desirable in relation to other aspects of lettuce cultivation.

Likewise, PPO activity has been implied to be involved in defence response and therefore reducing the browning potential by reducing PPO levels may increase the susceptibility to pathogens (Thipyapong, P. et al (2004) Planta 220, 105-117). Therefore, it was reasoned by the inventors that a more unbiased approach may be more successful in this respect. Such approach comprises the following steps:

1. Generation of a variant population of plants.

2. The set-up of an efficient phenotypic screen in which selection is based on a wound response-induced discolouration of the plant, in particular a leafy vegetable, more in particular lettuce, endive or witloof, which is channelled through PAL and/or PPO.

3. Characterisation of the variant plants modified in their wound-response with respect to post-harvest discolouration potential and absence of pleiotropic effects of the modification which compromise growing and processing of the plant, in particular a leafy vegetable, more in particular lettuce, endive or witloof, according to common practice.

The invention thus relates in one embodiment to an unbiased screening method for identifying, selecting and obtaining a plant showing a reduced wound-induced discolouration and post-harvest processing disorders such as enzymatic browning or pinking.

The invention in another embodiment relates to a more biased method that uses a substrate that is converted into a pigment by PPO. In this assay, the screen is specifically to PPO mutants. A suitable substrate is L-DOPA which is converted into the black pigment melanin.

The invention is illustrated herein referring to leafy vegetable, like lettuce, but can also be practised in the same way with other plants as indicated above.

"Variant plants" or "non-naturally occurring plants" are plants produced by human intervention. Examples of such plants are mutant plants, genetically modified plants produced, for instance, using recombinant methods, and plants resulting from intentional cross-breeding or selfing.

Mutant plants can, for example, be prepared as follows:

a) treating M0 seeds of a plant species to be modified with a mutagenic agent to obtain M1 seeds;

b) growing plants from the thus obtained M1 seeds to obtain M1 plants;

c) optionally repeating step b) and c) n times to obtain M1+n seeds;

d) germinating the thus obtained M1+n seeds, growing the plants from those seeds.

According to the invention non-naturally occurring plants are assayed for their wound-induced discolouration response. Plants that do not show or show a reduced discolouration response to wounding are selected. Then, progeny of the selected plants is grown and the wound-induced discolouration response is measured. Selected plants can be further cross-bred or inbred to produce other new varieties with the desired characteristics.

In order to create genetic variability, use can be made of mutagenesis. Several chemicals or physical treatments are know to the person skilled in the art which can be used to induce genetic mutations in plant species like lettuce. For example, one can treat seeds of lettuce in a solution containing different concentrations of a mutagen like ems. Ems alkylates primarily G residues of a DNA strand which during DNA replication causes pairing with T in stead of C. Therefore, GC basepairs change to AT basepairs at a frequency which is determined by the effective dose of ems and the activity of the mismatch repair system of the plant.

The effective dose of ems depends on the concentration used, the seed size and other physical properties and the time of incubation of the seeds in the ems solution. The seeds which have been treated with ems are typically called M1 seeds. As a consequence of the treatment, the tissues of the M1 seeds contain random point mutations in the genomes of their cells and those present in the subpopulation of cells which will form the germline tissue (germinal cells) will be transferred to the next generation which is called M2. Mutations or combinations thereof which are haplo-insufficient thereby causing sterility or which induce embryo lethality will not be transferred to the M2 generation.

A similar procedure as described above for the use of ems applies for other mutagenic agents as well. Suitable mutagenic agents are well-known in the art. Particularly useful are alkylating mutagenic agents, such as diethyl sulfate (des), ethyleneimine (ei), propane sultone, N-methyl-N-nitrosourethane (mnu), N-nitroso-N-methylurea (NMU), N-ethyl-N-nitrosourea (enu), sodium azide.

Alternatively, the mutations are induced by means of irradiation, which is for example selected from x-rays, fast neutrons, UV irradiation.

In another embodiment of the invention the non-naturally occurring plants are produced by means of genetic engineering, such as by means of use of chimeric oligonucleotides, homologous recombination, gene targeting, introduction of modified target genes which compete with the endogenous product, downregulation through RNA interference, etc.

The M2 population can be used in screening procedures aimed at wound response which is channelled through PAL and PPO. It is obvious to the skilled artisan that any population of plants that carries genetic variation can be taken as starting material for such phenotypic screen.

Preferably, the invention further relates to pyramiding alleles of reduced wound-induced discolouration response.

Production of M1 and M1+n seeds is suitably effected by means of self-pollination.

The invention further relates to obtaining non-naturally occurring plants or plant parts, which plants or plant parts show a reduced susceptibility towards physiological post-harvest processing disorders, such as enzymatic browning or pinking. The invention relates to plants or plant parts, which have in their genome genetic information which is responsible for the reduced susceptibility towards post-harvest processing disorders, such as enzymatic browning or pinking, and is found in the genome of a lettuce plant.

Progeny of the plants as claimed are also part of this invention. "Progeny" as used herein is intended to encompass all plants having the same or a similar reduced susceptibility towards post-harvest processing disorders, in particular enzymatic browning or pinking, as the original plants described herein and being derived therefrom in any way, such as by sexual reproduction, like self-fertilisation or cross-fertilisation with another plant of the same genus, or vegetative reproduction such as cutting, tissue culture, haploid culture, protoplast culture, protoplast fusion, or other techniques. Such progeny is not only the first generation of plants derived by one or more of these techniques, but also every further generation of plants derived by one or more of these techniques, provided that the derived plants have the reduced susceptibility.

The screening method of the invention may also be used to identify naturally occurring, wild type plants with the desired phenotype of reduced wound-induced discolouration. Once identified, these plants can be crossed or selfed and the non-naturally occurring progeny selected for the desired phenotype.

In order to carry out the phenotypic screen of the invention, a wound surface must be generated as the enzymatic discolouration reaction is induced upon wounding. Wounding is the irreversible disturbance of the natural plant, tissue and/or cell structure by methods like cutting, punching, slicing, abrasion, squashing, breaking, peeling, crushing, pressing, slashing, grinding, fluid injection, osmotic shock, detaching, mowing, shredding, rubbing and tearing.

Subsequently, a phenotypic characteristic must become manifest which is diagnostic for the pathway leading to tissue discolouration and which can be used very efficiently in a screen of the test plant population.

It was surprisingly found that such phenotypic characteristics can be obtained by taking leaf parts of lettuce plants and incubating them under very specific conditions which favour different forms of wound surface discolouration to occur. Subsequently, such assays can be applied to large numbers of test plants in order to select those plants which show a reduction of the wound-induced discolouration response.

One embodiment of this invention is based on the surprising finding that when discs from leaves, in particular lettuce leaves, are taken and incubated between wetted filter papers at 5° C., after approximately 4 days the formation of a pink dye at the edges of the leaf discs becomes apparent. Suitable filter paper is filter paper type 1450 CV, Ref no. 10 313 281 from Schleier & Schuell, Microscience GmbH, Dassel, Germany. Upon further incubation, the signal intensifies and after approximately one week the maximum intensity has been reached. The formation of the pink dye occurs specifically at wound surfaces.

The discolouration can be measured by scoring on a visual scale from 0, which means no browning or pinking, to 10, which means browning and pinking like a standard lettuce variety (*L. sativa*). In the present example the *L. sativa* variety 'Troubadour' is used as a standard for 10. If desired, pictures can be used for comparison to score the intermediate classes between 0 and 10. In addition, digital pictures can be made of the filter paper with the pink dye, followed by counting per leaf disc position the number of pixels with an intense pink colour. Using one of these measurements, simple statistical analyses like a t-test, well-known by persons skilled in the art, can be performed to establish whether a plant or group of plants is significantly less pinking than the standard, like cv. 'Troubadour'. The applied significance level of a one-sided test is 0.001.

For non-naturally occurring plants, the statistical comparison can be made between the pinking scores of the original variety, which is the best available standard, and the pinking scores of the individual non-naturally occurring plants and/or their offspring.

For finding the trait of the invention in existing plants, representative samples of varieties, breeding lines and/or gene bank accessions can be used. The statistical comparison can then be made between the pinking scores of the individual accession under investigation and the rest of the population. When statistically testing individuals for significantly less pinking multiple comparison tests may be needed to maintain proper overall significance levels, for example Dunnett's multiple comparison test with one standard (Dunnett C W, J. Amer. Statist. Assoc. 50: 1096-1121 (1955)).

Further, it was shown that the wound-induced discolouration response can be obtained using many different types of tissue of leaves of different developmental stages. For example, midrib tissue can also be induced to give this response upon wounding. When applied to different types of lettuces, such as butterhead, iceberg, cos, batavia or oakleaf, no individual accessions were found that showed significantly less pinking than the rest of the investigated population.

It was further demonstrated according to the invention that a specific inhibitor of PPO, L-cysteine, when applied during the reaction, strongly suppressed the formation of the pink dye. In addition, it was found that the formation of the pink dye was inhibited by cinnamaldehyde, which is an inhibitor of PAL activity and browning of fresh cut lettuce (Fujita, N. et al (2006) Biosci. Biotechnol. Biochem. 70, 672-676). These findings show that the pink discolouration response of lettuce is PAL and PPO dependent.

Enzymatic browning of fresh cut lettuce is known to be very effectively prevented by the application of a brief heat shock. The observed effect can be explained by assuming re-routing of protein biosynthesis from the phenyl propanoid pathway towards heat shock proteins thereby reducing the metabolic flux towards the formation of polyphenols.

Alternatively, the effect may be explained by assuming that the enzymes involved in polyphenol oxidation, such as PPO and POD, are inactivated by the heat shock treatment. When the heat shock is applied to lettuce which is subsequently assayed for the pinking response, it was shown that this response, like the enzymatic browning, was effectively inhibited. This demonstrates that the pinking response of lettuce which is part of this invention is physiologically very similar to the well known enzymatic browning response.

This finding was further substantiated by applying L-cysteine as a reducing agent. L-cysteine, besides being an inhibitor of PPO, is also known to react with coloured o-quinones and convert them back into colourless diphenols in a chemical reduction reaction. When the pink dye formed by lettuce leaf discs is treated with L-cysteine, it was demonstrated that the pink compound was converted into a colourless compound. It seems therefore likely that the pink dye is an o-quinone formed by PPO.

This was corroborated by the finding that reducing agents like ascorbic acid or glutathion also convert the pink dye into a colourless compound.

In addition, when plants, which are taken from the field which show pinking, are treated with L-cysteine, the pink discolouration is also eliminated. This demonstrates that the leaf disc pinking response is representing the natural occurring pinking phenomenon which can sometimes be seen on plants growing under field conditions.

A further embodiment of this invention is based on the following experiment. Parts of a lettuce leaf of a head are produced by cutting and incubated at 16° C. in air. As a response the wound surface turns brown after approximately 4 days. Especially at the wound surface of the main vein the browning can clearly be observed. Furthermore, the browning reaction can also be observed at the whole plant level upon damaging leaves by cutting or abrasion.

All of these browning reactions can completely be inhibited by L-cysteine, an inhibitor of PPO, which demonstrates that these phenotypes are manifested through PPO activity and therefore can be considered diagnostic for post-harvest browning as observed during processing and packaging of lettuce.

These wound-induced browning reactions can be generated in an efficient manner which can be exploited in a phenotypic screening procedure to identify plants that are reduced in wound-induced browning potential.

A further embodiment of this invention is based on the discolouration at wound surfaces of lettuce tissues induced by applying substrates which can be converted by the phenol oxidising enzymes into coloured compounds.

For example, when lettuce leaf discs are incubated with the PPO substrate L-3,4-dihydroxyphenylalanine (L-DOPA), a dark brown to black discolouration is observed at the wound surface which is the manifestation of the formation of melanine through PPO. When L-cysteine was applied simultaneously, the black discolouration was completely inhibited which confirms the assumption that this discolouration is PPO mediated.

Although L-DOPA is not considered to be a natural substrate for lettuce PPO it can be useful in assays aimed at the identification of plants that show reduced wound-induced discolouration.

In a similar manner as described for L-DOPA other substrates can be applied in order to raise a discolouration response. These include but are not limited to chlorogenic acid, isochlorogenic acid, L-tyi-osine, and catechol.

Figure 1:
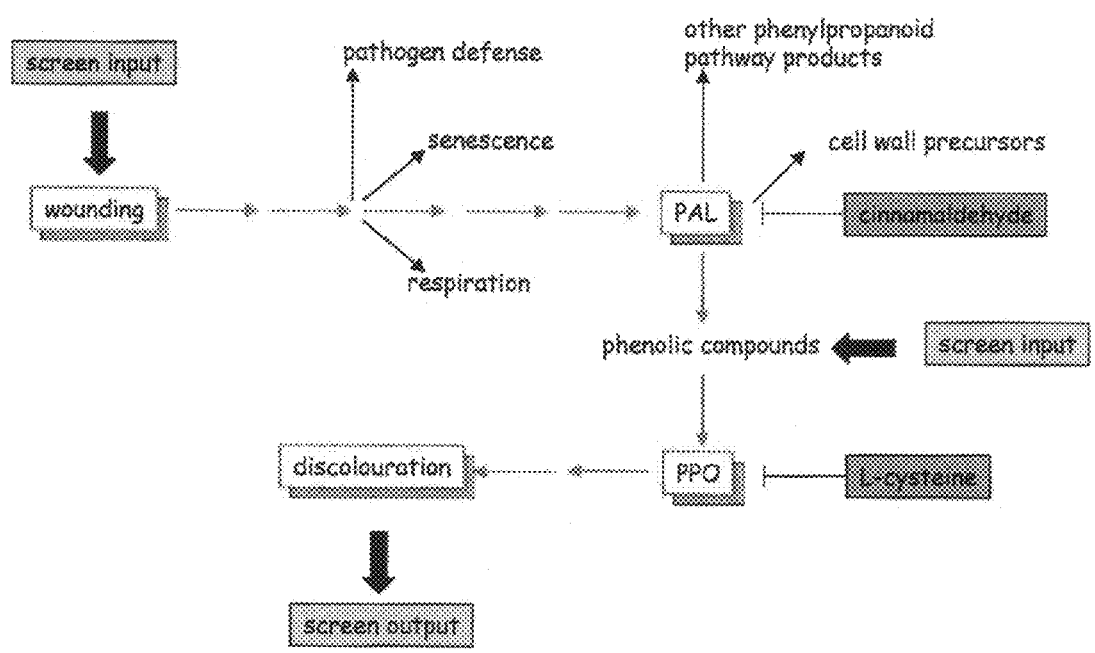
FIG. 1: Schematic outline of the rationale behind the design of the mutant screening procedure of lettuce populations for reduced post-harvest enzymatic discolouration. The input signal of the screen is wounding of leaf tissue which is sensed by the plant and which generates a divergent signalling response leading to a number of physiological processes including senescence, respiration and tissue discolouration. This input signal can be combined with the application of phenolic compounds as PPO substrates.

Taken together, the formation of the different dyes at wound surfaces generated in plants monitors modifications in a pathway starting by the induction of a wound signal, channelled through PAL and PPO and leading to discolouration. As described, these wound-induced discolouration reactions can readily be assessed by visual inspection which allows a very efficient screening procedure. The rationale underlying the method described by this invention is illustrated in FIG. 1.

According to this invention it was thus found that the wound-induced discolouration pathway of leaf discs in vitro largely overlaps with the wound-induced discolouration of lettuce processed at industrial scale and can therefore be considered diagnostic for this process. This is corroborated by the notion that inhibitors of PAL or PPO inhibit the enzymatic browning of processed and packaged lettuce under practical, industrial conditions. Importantly, as the procedure comprises the inducing step i.e. wounding and one of the final metabolic conversions mediated by PPO, the procedure allows capture of all genetic factors directly or indirectly involved in this physiological process. Moreover, as this response can be generated using a whole range of leaf tissues of leaves of different developmental stages, screens can be targeted towards these different stages or tissues when considered relevant.

Plants that have been identified as being modified with respect to the physiological process leading from wounding to a PAL- and PPO-dependent discolouration based on one or more of the phenotypic assays described above can be further characterised. Such characterisation can be done at different levels e.g. at the molecular, biochemical, physiological and phenotypic level.

It is obvious to those skilled in the art that variable levels of discolouration may be observed which may reflect either the presence of different mutant loci or different allelic forms of identical loci affecting the discolouration trait in the original population.

In case of recessive mutations these two possibilities can easily be distinguished by carrying out allelism tests which comprise the crossing of the two mutant plants and determining the phenotype of the hybrid. In case of allelism of the mutations, the reduced discolouration trait will be apparent in the F1 whereas in case the phenotype in the mutants is determined by different recessive loci this will not be the case.

As random mutagenesis was applied to generate the starting population, mutations in the genetic background may also contribute to the variation of the phenotype under the experimental conditions. In order to discriminate between single mutations of different strengths and a combined effect of mutations in the genetic background, backcrosses should be performed to create uniform genetic backgrounds for the different reduced discolouration events.

Such procedure is further relevant in order to determine whether mutations at specific loci involved in wound-induced discolouration display pleiotropic effects.

The M2 plants thus selected on the basis of a reduced discolouration response are used to grow M3 seeds. Subsequently, the inbred lines descending from the reduced discolouration events are re-evaluated for their reduced response wounding. In addition, the reduced browning or pinking can be assessed in different genetic backgrounds and under different conditions of crop cultivation and processing.

Biochemical studies can be performed to address questions related to the pathways affected by the genetic modification. Molecular studies can be performed to determine if candidate genes putatively involved in the enzymatic browning or pinking response like genes encoding PAL, PPO or peroxidases have been modified. Genetic analysis will subsequently be carried out to demonstrate if the modification found in a candidate gene is causative with respect to the altered phenotype.

Although induced mutagenesis is the preferred method to be used in this invention, it is known to the person skilled in the art that technology exists to modify gene targets residing in the genome of a plant in a specific manner. For example, chimeric oligonucleotides have been demonstrated to be effective mutagens with a specific mode of action.

Another approach is to modify gene targets through homologous recombination or gene targeting. Using such approach, a fragment of a gene is exchanged by an introduced DNA fragment containing a desired modification. Transgenic approaches are also feasible in which modified target genes are introduced which compete with the endogenous product. This may lead to dominant negative effects. Moreover specific downregulation of the expression of genes is feasible through RNA interference.

Where mutagenic oligonucleotides, gene targeting or transgenic approaches are used to modify a genetic factor involved in wound induced discolouration response, obviously, the primary structure of the relevant genes should be known.

A further parts of this invention relates to lettuce mutants and progeny derived therefrom which were identified on the basis of the wound-induced pink discolouration of lettuce leaf discs. Applying this pinking assay to plants of an M2 population which contain random, ems-induced mutations resulted in the identification of a number of mutants which showed a significant reduction of the pinking response as compared to the control plants which do not contain the ems-induced mutations.

Most of such mutants showed a dwarfed and often chlorotic phenotype. It was however surprisingly found that some mutants with a reduced pinking response showed a normal growth habitus, i.e. a size, shape, growth and colour very much similar to the control plants.

When progeny plants of this particular mutant grown from seeds obtained through self-fertilisation are assayed for pinking, a similar reduction as found for the originally identified mutant is observed. This demonstrates that a reduced pink discolouration response can be heritable and caused by a modification of the genome.

A further surprising finding was the fact that when the progeny plants are grown to maturity and tested for enzymatic browning of wounded midrib tissue, this response is also strongly inhibited.

This shows that the leaf disc pinking assay which is part of this invention is causally related to enzymatic browning in lettuce and that the pinking assay can be used to predict the level of enzymatic browning of a mature lettuce plant.

Therefore, the leaf disc pinking assay can be used as a selection tool to identify lettuce plants with a reduced enzymatic browning potential. Such tool can be used to identify lettuce plants with reduced enzymatic browning potential from any kind of plant population irrespective of the cause of the genetic variation which resides in such population. For example, in addition to ems populations, one can use natural accessions or breeding populations.

One or more of the screening methods provided by this invention can be applied to any leafy vegetable species for which post-harvest processing quality needs improvement. Therefore, this invention can in addition to cultivated lettuce also be applied to other plant species belonging to the Asteraceae, such as wild species of the *Lactuca* genus. Furthermore, the invention can be applied in particular to plant species belonging to the plant genus *Cichorium* to which species like endive (*Cichorium endivia*), chicory and witloof chicory (*Cichorium intybus*) belong.

The present invention relates to a phenotypic feature that can be detected in a plant by performing one of the screening methods that are disclosed herein. Plants of the invention are those plants which compared to a control plant show the absence of or a reduction in wound-induced surface discolouration. The presence of the feature is determined by means of one or more of three discolouration tests, namely the occurrence of pinking or browning or the ability to convert the substrate L-DOPA to melanin. A plant of the invention is a plant which in at least one of these tests shows a discolouration that is at least reduced as compared to a control.

The "control" as used herein is any plant of which it is known that it shows one or more of the discolouration reactions pinking, browning and conversion of L-DOPA to melanin, which reactions can be inhibited by L-cystein or cinnamaldehyde. Suitably a plant is used of which a leaf disc when incubated between wetted filter paper at 5° C. for 7 days shows pink discolouration around the edges of the disc.

According to the invention, plants were identified and selected that show no or a significantly reduced wound-induced surface discolouration. Progeny of seeds of these plants were deposited on Oct. 10, 2006 and Jan. 3, 2007 under the terms of the Budapest Treaty with the National Collections of Industrial, Marine and Food Bacteria (NCIMB) in Bucksburn, Aberdeen AB21 9YA, Scotland, UK, which is an acceptable depository recognized under the Budapest Treaty, and assigned NCIMB accession numbers 41441 and 41454, respectively, listed in Table 1. Deposited seeds will be irrevocably and without restriction or condition released to the public during the term of any patent issued from this application. Details about seed descendance of the deposits are given in Example 4 and in Example 6. These deposits are made because they have the single specific characteristic of no or significantly reduced wound-induced discolouration. They were not tested for DUS-criteria for variety registration, i.e. distinguishability, uniformity, stability on all registration characteristics, and are not expected to meet these criteria in any way.

TABLE 1

| Plant no. | Internal Ref. (=NCIMB Ref.) | NCIMB Accession No. | Date of Deposit |
|---|---|---|---|
| 06D.210202 | 06D.863B2 | 41454 | 3 Jan. 2007 |
| 05D.202539 | 07G.9979 | 41441 | 10 Oct. 2006 |

EXAMPLES

Example 1

Genetic Modification of Lettuce Using Ems

Approximately 2000 seeds of the lettuce varieties Troubadour, Apache, Yorvik and Roderick were incubated in an aerated solution of either 0.05% (w/v) or 0.07% (w/v) ems during 24 hours at room temperature. After the ems treatment the M1 seeds were rinsed water and planted in a greenhouse at 20° C. at 16 hours light, 8 hours dark regime to grow the mature plants and to induced bolting and flowering in order to produce M2 seeds. After maturation, M2 seeds were harvested, bulked and stored until further use. The mutation frequency was estimated on the basis of the relative number of individual plants with a bleached phenotype which are disturbed in the chlorophyll biosynthesis.

Example 2

Development of a Phenotypic Screen Diagnostic for the Wound-Induced Discolouration of Lettuce Based on Pink Pigment Formation A phenotypic assay was developed in which leaf discolouration of lettuce induced by wounding can readily be assessed. This approach allows young plant screening for discolouration. Leaf discs of 5 mm diameter were taken from young or mature plants and placed between wetted filter papers in a tray. The system was incubated at 5° C. for 7 days. During the incubation a pink dye developed at the wound site of the leaf disc which became clearly visible as a printed circle on the filter paper (FIG. 2).

In order to demonstrate that the production of the pink dye requires an active phenylpropanoid pathway, the effect of inhibitors of PAL (cinnamaldehyde, FIG. 3) and PPO (L-cysteine, FIG. 4) were tested in this assay. When cinnamaldehyde was applied during the assay, the pink discolouration was completely inhibited at a concentration of 0.01% or higher.

A similar result was obtained using L-cysteine at a concentration of 0.001% and higher, while other amino acids like L-leucine or L-alanine did not show any effect. This demonstrates that L-cysteine can inhibit the pinking response of the lettuce leaf discs and that the inhibitory effect of L-cysteine is specific.

In order to demonstrate that L-cysteine is indeed acting as an inhibitor of PPO activity in this system, the lettuce leaf discs were incubated with the PPO substrate L-3,4-dihydroxyphenylalanine (L-DOPA). Although L-DOPA is not considered to be a natural substrate for lettuce PPO, a dark brown to black discolouration was observed at the wound surface which is the manifestation of the formation of melanin through PPO. When 1 mM or a higher concentration of L-cysteine was applied simultaneously, the discolouration was completely inhibited as shown in FIG. 5.

The lettuce leaf disc pinking response was further characterised by applying a heat shock before inducing the wound response. Detached leaves were incubated during 90 seconds at 21, 40, 50 and 60° C. After this treatment leaf discs were taken and assayed for pinking. The pinking response was completely inhibited when the heat shock was carried out at a temperature of 50° C. or higher. This result is shown in FIG. 6.

As L-cysteine is known to react with o-quinones, which are PPO products, by converting them back into colourless diphenols, the effects of L-cysteine on the pink dye coming from lettuce leaf discs was determined. In parallel the effect of L-cysteine was determined on the melanin formation upon incubation with L-DOPA.

Leaf discs were taken and incubated according to the procedures described above. After the wound response was completed, a concentration series of L-cysteine was added to the leaf disc and the change in colour was monitored. The result is shown in FIG. 7. The experiment clearly demonstrated that L-cysteine was converting the pink dye back into a colourless compound whereas the black melanin formed in the L-DOPA assay was not affected by the L-cysteine. This demonstrates that the pink dye is very likely an o-quinone which is formed by the lettuce polyphenol oxidation system.

To demonstrate that the observed in vitro response reflects a response which is physiologically relevant the L-cysteine based discolouration was applied to field-grown plant material. This was carried out by harvesting a leaf from a field-grown lettuce plant which showed severe pinking symptoms along the veins. This is typically observed when plants have been stressed, for example by conditions of severe water logging. The leaf was used to prepare leaf discs which were incubated immediately by 1 mM L-cysteine. After approximately 30 minutes incubation at room temperature, the pink discolouration disappeared as shown in FIG. 8.

Taken together, these experimental data show that lettuce leaf discs can be induced by wounding to produce pink discolouration which is PAL and PPO dependent. This phenotype allows an efficient and effective screening procedure for lettuce mutants which have a modified wound response induced discolouration channelled through PAL, PPO or both.

Example 3

Screening for Mutants with a Reduced Wound-Induced Discolouration

In order to identify lettuce mutants with low wound-induced enzymatic browning or pinking potential, the leaf disc assay described in Example 2 was applied to plants of a lettuce mutant population.

12000 Plants were grown in a greenhouse (sowing on day 1, planting on day 22; growing under regular lettuce grower's conditions) and from each individual plant a leaf disc was taken (sampling from day 49 onward) and incubated as pools of (on average) 25 samples between wetted filter papers at 5° C. for 7 days. A visual score was given to each leaf disc depending on the intensity of the pink discolouration. On the basis of this assessment, plants were selected of which the leaf discs showed no or a relatively low degree of wound surface discolouration. The plant with hardly visible traces of discolouration was numbered 06D.210202.

Figure 9:
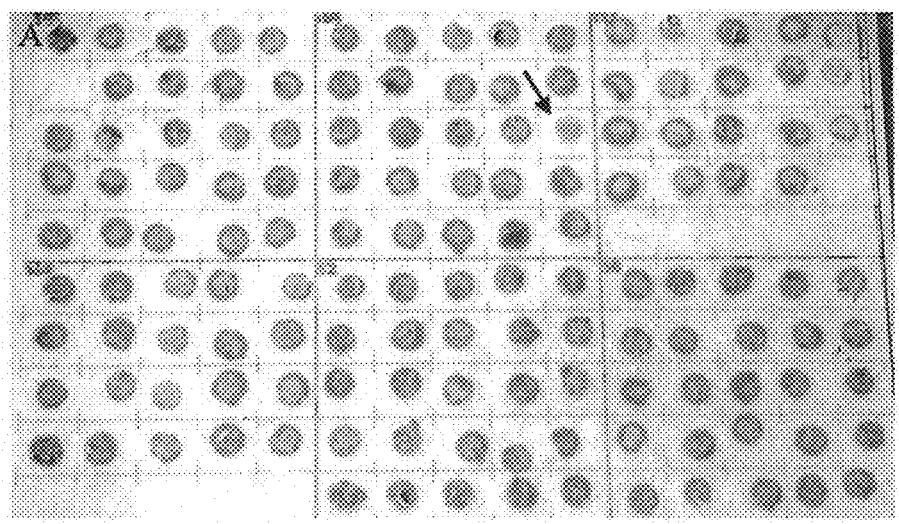
Figure 9:
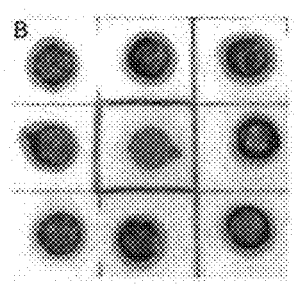

Of the 12000 plants, 1 plant was finally selected which showed only traces of discolouration which were hardly visible and 12 which showed a relatively low level of discolouration. The result of one of these assays is shown in FIG. 9.

The discolouration assay was repeated for the initially selected 12 individuals and for most individual cases the original result was confirmed. Only the confirmed individuals were selected for further analysis and seed production.

Example 4

Screening for Mutants with Reduced Wound-Induced Discolouration

In order to identify lettuce mutants with low wound induced enzymatic browning potential the leaf disc assay described in Example 2 was applied to plants of a lettuce mutant population. 8500 plants were grown in a greenhouse until 3 weeks old (6-8 leaf stage) and from each individual plant a leaf disc was taken and incubated between wetted filter papers at 5° C. for 7 days.

A visual score was given to each leaf disc depending on the intensity of the pink discolouration. On the basis of this assessment, plants were selected of which the leaf discs showed no or a relatively low degree of wound surface discolouration. Of the 8500 plants 8 plants were selected which did not show any visible discolouration and 10 showed a relatively low discolouration. The discolouration assay was repeated for the 18 individuals that were initially selected and for most individual cases the original result was confirmed. Twelve individuals are shown in FIG. 10. Only the confirmed individuals were selected for further analysis and seed production. One mutant plant without pleiotropic side-effects (e.g. bleaching, dwarfing) was given number 05D.202539. The seed produced by selfing of this plant was numbered 05D.810596. The seed produced by selfing of three plants grown from seeds of 05D.810596 was numbered 07G.9979 and deposited at NCIMB. The NCIMB-number is 41441 (deposited on 10 Oct. 2006).

Example 5

Phenotypic Analysis of the Selected Mutants Showing Reduced, Wound-Induced Discolouration Of the 12 mutants selected from the screen presented in Example 3, 6 showed a strong reduced growth phenotype and bleaching. Other mutants developed normally i.e. according to the type of the starting population of the mutagenesis experiment.

The dwarfed and bleached mutants are probably disturbed in chloroplast function. As PPO resides in these cellular organelles this may explain the relatively low response in the leaf disc assays. As such pleiotropic mutations are undesirable, these mutants were considered to be less relevant.

The mutant plant 06D.210202, which showed the strongest reduction of leaf disc discolouration, showed a normal phenotype and the mutation is therefore considered specific for the discolouration without strong pleiotropic effects.

Example 6

Confirmation of the Near Absence of Discolouration Phenotype in Offspring

To demonstrate that the reduced discolouration of lettuce mutants like plant 06D.210202 from Examples 3 and 5 is caused by a genetic effect generated by the mutagenesis treatment described herein, seed were produced by selfing. The seed produced by selfing of plant 06D.210202 was numbered 06D.819784. The seeds were germinated in soil and the plants were tested for discolouration using the leaf disc pinking assay.

This experiment clearly showed that the altered phenotype had a genetic basis as all progeny plants showed a similar phenotype i.e. a strong reduction in pink discolouration, like the mutant which was used to produce the seeds. This result is illustrated in FIG. 11.

The seed produced by selfing of three plants grown from seeds of 06D.819784 was numbered 06D.863B2 and deposited at NCIMB. The NCIMB-number is 41454 (deposited on 3 Jan. 2007).

Example 7

Development of a Phenotypic Screen Diagnostic for the Wound-Induced Discoloration of Lettuce Based on Brown Pigment Formation Lettuce plants were grown to maturity and parts of outer leaves were taken by cutting discs from the rib tissue. The discs were incubated on wetted filter paper at 16° C. After approximately 72 hours, the wound surface had turned brown. In the presence of 10 mM L-cysteine the browning response was inhibited indicating that the observed discolouration is PPO mediated. A representative outcome of such experiment is shown in FIG. 12.

As the response as displayed in FIG. 12 is a PPO mediated browning response, the screening procedure as described in this example can considered to be effective and unbiased in order to screen for mutants showing reduced brown discolouration which occurs during the processing of lettuce.

Example 8

Development of a Phenotypic Screen Diagnostic for the Wound-Induced Discolouration of Lettuce Based on the conversion of L-3,4-dihydroxyphenylalanine (L-DOPA) into a Black Pigment Called Melanin In addition to assays which address wound-induced discolouration in a broad sense, the method according to this invention also allows to screen in a more specific manner for mutants which have a reduced PPO activity. A phenotypic assay which is indicative for PPO activity was developed by using leaf discs which were incubated in the presence of 1.5 mM L-DOPA. As a black discolouration became apparent it can be concluded that L-DOPA can readily be converted by the polyphenol oxidising system at the wound surface of lettuce leaves into a black pigment called melanine. L-DOPA is converted by PPO into the reactive L-DOPA-quinone which is converted non-enzymatically via dopachrome and indol quinone into the black melanin.

Furthermore, it was shown that the reaction can be inhibited by adding 1 mM L-cysteine during the reaction (FIG. 5). Therefore, this assay enables the identification of mutants which are modified in the ability to mount a PPO activity at a wound surface of a leaf. The response of lettuce leaf discs to the presence of L-DOPA can be observed both in solution as well as between wetted filter papers as shown in FIG. 13.

Example 9

Assessing the Offspring of a Mutant Showing a Near Absence of Discolouration for Reduced Browning Response Using the Rib Disc Browning Assay To demonstrate that the reduced discolouration of lettuce mutants like plant 06D.210202 from Examples 3, 5 and 6, which is significantly reduced in pink discolouration of wound surfaces of leaf discs is also effectively reduced in the wound-induced browning response, a number progeny plants were grown to maturity.

At this stage of development, 3 midrib discs are taken from the outer leaves of a number of progeny plants. These rib discs are incubated according to the procedure described in Example 7. It is shown that the progeny plants of the mutant which were earlier shown to be strongly reduced in wound-induced pink discolouration are also strongly reduced in wound-induced midrib browning. The result of this experiment is shown in FIG. 14.

Example 10

Assessing the Offspring of a Mutant Showing Near Absence of Discolouration for Reduced Browning Response Using Fresh Cut Lettuce Heads Packaged in Plastic Bags Mature heads of the lettuce plants grown from seed 06D.819784 from Example 6, which is significantly reduced in pink discolouration of wound surfaces of leaf discs, were cut into pieces using a knife and packaged in a plastic bag containing an ambient atmosphere. Control plants which show a normal leaf disc pink discolouration response were treated in an identical manner. The bags were stored at 4° C. during 6 days after which the leaf material was assessed for its browning response.

It is shown by this experiment that the progeny plants of the mutant which were earlier shown to be strongly reduced in wound-induced pink discolouration are also strongly reduced in wound-induced midrib browning when processed and stored in plastic bags using an ambient atmosphere. The result of this experiment is shown in FIG. 15.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

I claim:

1. A lettuce plant showing a reduced wound-induced surface discolouration trait,
   wherein the plant has genetic information in its genome which is responsible for the reduced wound-induced surface discolouration trait,
   wherein reduced wound-induced surface discolouration is as compared with a control plant not showing the reduced wound-induced surface discolouration trait as indicated by a leaf disc from the control plant showing pink discolouration at the edges when incubated between two sheets of wetted filter paper for 7 days at 5° C., and
   wherein the genetic information which is responsible for the reduced wound-induced surface discolouration trait is as found in a lettuce plant, representative seed of which was deposited under NCIMB accession number NCIMB 41454 or NCIMB 41441.

2. A seed of the plant of claim 1, wherein a plant grown from said seed has the reduced wound-induced surface discolouration trait.

3. A plant, or part thereof, produced by propagation of and/or breeding with the plant of claim 1, and having the reduced wound-induced surface discoloration trait.

4. Progeny plant of a lettuce plant of claim 1 having the reduced wound-induced surface discoloration trait.

5. Progeny plant of a lettuce plant of claim 1 having the reduced wound-induced surface discoloration trait and all the morphological and physiological characteristics of a lettuce plant, representative seed of which has been deposited under NCIMB 41454 or NCIMB 41441.

6. Propagation material from which a lettuce plant of claim 1 can be produced.

7. A method of producing a lettuce plant, or part thereof, having the reduced wound-induced surface discoloration trait, wherein the plant has genetic information in its genome which is responsible for the reduced wound-induced surface discoloration trait, wherein the genetic information is as found in a lettuce plant representative seed of which was deposited under NCIMB accession number NCIMB 41454 or NCIMB 41441; said method comprising producing progeny from the plant of claim 1, or part a thereof.

8. A plant produced from the method of claim 7, having the reduced wound-induced surface discoloration trait and having genetic information in its genome which is responsible for the reduced wound-induced surface discoloration trait, wherein the genetic information is as found in a lettuce plant, representative seed of which was deposited under NCIMB accession number NCIMB 41454 or NCIMB 41441.

9. The lettuce plant of claim 1 having all characteristics of a lettuce plant grown from seed deposited under NCIMB accession number NCIMB 41454 or NCIMB 41441.

10. The plant of any one of claim 1, 3, 4, 5, 8, or 9, or the seed of claim 2, or the propagation material of claim 6, or the method of claim 7, wherein the representative seed is that which was deposited with the NCIMB under accession number NCIMB 41454.

11. The plant of any one of claim 1, 3, 4, 5, 8, or 9, or the seed of claim 2, or the propagation material of claim 6, or the method of claim 7, wherein the representative seed is that which was deposited with the NCIMB under accession number NCIMB 41441.

* * * * *